US009030034B2

(12) United States Patent
Grieser et al.

(10) Patent No.: US 9,030,034 B2
(45) Date of Patent: May 12, 2015

(54) STATIONARY POWER PLANT, IN PARTICULAR A GAS POWER PLANT, FOR GENERATING ELECTRICITY

(75) Inventors: Jens Grieser, Sohnstetten (DE); Jurgen Berger, Gerstetten (DE); Stephan Bartosch, Freiburg (DE)

(73) Assignee: SteamDrive GmbH, Heidenheim (DE)

(*) Notice: Subject to any disclaimer, the term of this patent is extended or adjusted under 35 U.S.C. 154(b) by 0 days.

(21) Appl. No.: 13/880,936

(22) PCT Filed: Jan. 31, 2012

(86) PCT No.: PCT/EP2012/000405
§ 371 (c)(1),
(2), (4) Date: Jul. 12, 2013

(87) PCT Pub. No.: WO2012/107177
PCT Pub. Date: Aug. 16, 2012

(65) Prior Publication Data
US 2013/0277968 A1 Oct. 24, 2013

(30) Foreign Application Priority Data

Feb. 10, 2011 (DE) .......................... 10 2011 010 974

(51) Int. Cl.
*F02D 25/00* (2006.01)
*F01K 23/10* (2006.01)
(Continued)

(52) U.S. Cl.
CPC .............. *F01K 23/10* (2013.01); *F01K 23/065* (2013.01); *F02B 41/10* (2013.01); *F02B 63/04* (2013.01);
(Continued)

(58) Field of Classification Search
CPC .................................. F02B 63/04; F02G 5/04
USPC .............................................. 290/1 A, 2, 4 D
See application file for complete search history.

(56) References Cited

U.S. PATENT DOCUMENTS 4,503,337 A 3/1985 Häfner
2007/0007771 A1 1/2007 Biddle
(Continued)

FOREIGN PATENT DOCUMENTS

DE 10 2010 000 487 8/2011
EP 1 243 758 9/2002
(Continued)

OTHER PUBLICATIONS

English Translation of International Preliminary Report on Patentability.

*Primary Examiner* — Tho D Ta
(74) *Attorney, Agent, or Firm* — Farjami & Farjami LLP

(57) ABSTRACT

The invention concerns a stationary power plant, in particular a gas power plant, to generate electricity;
  having an internal combustion engine, comprising a fuel medium inlet and an exhaust gas outlet, whereas an exhaust-gas flow of the internal combustion engine is discharged via the exhaust gas outlet;
  having an electrical generator, which is driven by the internal combustion engine to generate electricity, and which is coupled or can be coupled to an electrical grid, in order to feed the generated electricity into said grid;
  having a fuel medium supply, which is connected to the fuel medium inlet; wherein
  a steam circuit, in which a working medium is circulated by means of a feed pump, is provided, comprising a heat exchanger arranged in the exhaust gas flow, by means of which waste heat of the exhaust gas flow is transferred to the working medium for partially or completely evaporating the working medium, further comprising a condenser, in which the working medium partially or completely condenses.
The invention is characterized in that
  a reciprocating piston expander is provided in the steam circuit, in which the working medium expands to produce mechanical work, and
  the reciprocating piston expander is connected mechanically to the internal combustion engine and/or the electrical generator by means of a releasable clutch.

14 Claims, 1 Drawing Sheet

(51) Int. Cl.
  *F01K 23/06* (2006.01)
  *F02B 41/10* (2006.01)
  *F02B 63/04* (2006.01)
  *F02G 5/02* (2006.01)
  *F24D 10/00* (2006.01)
  *F01N 5/02* (2006.01)
  *F02B 75/24* (2006.01)

(52) U.S. Cl.
  CPC .............. *F02G 5/02* (2013.01); *F24D 2200/26* (2013.01); *Y02T 10/163* (2013.01); *Y02T 10/166* (2013.01); *F24D 10/00* (2013.01); *Y02E 20/14* (2013.01); *F01N 5/02* (2013.01); *F02B 75/24* (2013.01)

(56) References Cited

U.S. PATENT DOCUMENTS

2010/0083919 A1* 4/2010 Bucknell .................... 123/41.21
2010/0242476 A1   9/2010 Ast

FOREIGN PATENT DOCUMENTS

| EP | 2 055 912 | 5/2009 |
| JP | 58-181960 | 12/1983 |

* cited by examiner

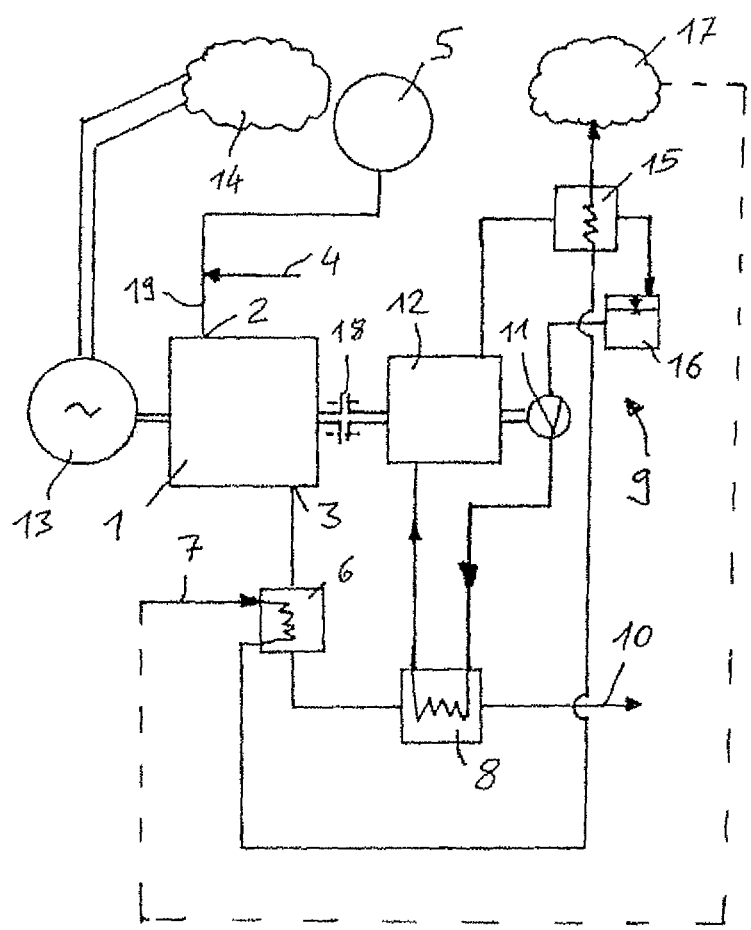

STATIONARY POWER PLANT, IN PARTICULAR A GAS POWER PLANT, FOR GENERATING ELECTRICITY

This is a U.S. national phase application, which is based on, and claims priority from, PCT application Serial No. PCT/EP2012/000405, filed Jan. 31, 2012, which claims priority from foreign application Serial No. 10 2011 010 974.9, filed Feb. 10, 2011, in Germany.

The present invention concerns a stationary power plant for generating electricity, in particular a gas power plant, in detail having the features of the preamble of claim 1. In a particularly advantageous embodiment, the power plant is designed as a combined heat and power unit (CHP), with a cogeneration of heat and power.

Power plants, in particular combined heat and power units, are generally modular installations for generating electrical energy and preferably heat, which can be operated for instance directly at the location of the heat consumption or that can feed useful heat into a local heating network or a district heating network. Its mode of operation is based on the cogeneration principle.

Generally an internal combustion engine can be considered as a drive machine for the electrical generator, preferably a diesel or gas engine. Forms of embodiment having a gas turbine are also disclosed.

Very high degrees of efficiency can be achieved thanks to the combination of the waste heat recycling for generating a heat flow and producing electrical power by driving the generator with the internal combustion engine generating the waste heat which enables to use the input primary energy up to 80-90 percent. This means in comparison to traditional power plants, such as steam power plants, a saving of up to 40 percent of primary energy. Such stationary power plants, which usually have electrical powers between 5 kW and 5 or 10 MW, are hence considered as almost ideal. Nevertheless, a further increase in the degree of efficiency represents even better usage of primary energies available. The problem with such further improvements is still that a more complex configuration of the very heavy-duty mechanical systems potentially limits the very high availability of known power plants of the type mentioned initially.

US 2007/0007771 A1 discloses an internal combustion engine, whose waste heat is used in a steam circuit with a turbine and a condenser. The turbine drives a generator.

The postpublished patent application DE 10 2010 000 487 A1 discloses the use of the waste heat of a drive unit of combined heat and power units in which an internal combustion machine and an expansion combustion machine can drive together a crankshaft by means of a direct mechanical coupling.

US 2010/0242476 A1 is referred to for other state of the art.

The object of the present invention is to further optimise a stationary power plant of the type above mentioned as regards the degree of efficiency and the energy yield. Consequently, the existing advantages can still be used unaltered and the optimisation should absolutely not restrict the availability of the respective power plant.

The object of the invention is solved by a stationary power plant exhibiting the features of claim 1. Advantageous and particularly appropriate embodiments of the invention are disclosed in the dependent claims.

A stationary power plant according to the invention, which is designed in particular as a gas power plant, enables the production of electricity and includes an internal combustion engine, by means of which an electrical generator is driven. The internal combustion engine contains a fuel medium inlet and an exhaust gas outlet. A fuel medium supply, in particular a gas supply, is connected to the fuel medium inlet to feed the combustion medium, in particular gas, via the fuel medium inlet into the combustion chamber, in particular in the form of one or several expansion cylinders.

An exhaust gas flow of the internal combustion engine is evacuated via the exhaust gas outlet whereas the exhaust gas flow contains waste heat.

The electrical generator, which is driven by the internal combustion engine, is coupled to an electrical grid or can be coupled thereto, so as to feed the electricity generated by said generator into said electrical grid. It goes without saying that a rectifier or a converter or other electrical components can be provided between the generator and the electrical grid.

If the power plant works according to the cogeneration principle, the internal combustion engine is cooled by means of a heat carrier flow, in particular a cooling water flow, whereas the waste heat of the internal combustion engine is fed to the heat carrier flow. The waste heat of the internal combustion engine can hence be transmitted directly in the internal combustion engine properly speaking, in particular inside the engine housing, to the heat carrier flow and/or can be drawn from the exhaust gas flow generated by the internal combustion engine and fed to the heat carrier flow, for instance via a heat exchanger in the exhaust gas flow. The waste heat of the internal combustion engine absorbed from the heat carrier flow is then fed into a district heating network, local heating network, process heating network or another heat recovery system.

A steam circuit is provided according to the invention for optimal usage of the waste heat, which is still contained in the exhaust gas flow, a circuit in which a working medium is circulated by means of a feed pump. The steam circuit includes a heat exchanger located in the exhaust gas flow, by means of which waste heat of the exhaust gas flow is transferred to the working medium for partially or completely evaporating the working medium. This first heat exchanger hence could also be designated as evaporator. Besides, the steam circuit comprises a reciprocating piston expander in which the working medium expands to produce mechanical work, as well as a condenser, in which the working medium partially or completely condenses.

According to the invention, the reciprocating piston expander is mechanically coupled to the internal combustion engine and/or to the electrical generator for driving said generator. Additionally or alternately, the reciprocating piston expander can also be coupled to a second additional electrical generator.

The coupling of the reciprocating piston expander to the internal combustion engine and/or to the electrical generator, which is driven by the internal combustion engine, is advantageously provided by means of a releasable clutch. This enables to release the clutch easily in case of problems with the steam circuit or the reciprocating piston expander so that the power plant can be further operated as before without additional waste heat recycling. Accordingly, the availability of the power plant is not restricted. It is further possible to select without availability restrictions the maintenance intervals of the steam circuit or of the reciprocating piston expander independent of the maintenance intervals of the other components of the power plant.

In a particularly advantageous embodiment, the reciprocating piston expander includes a crankshaft, which is connected to a crankshaft of the internal combustion engine, in particular directly via the clutch.

The internal combustion engine is advantageously designed as a gas engine, whereas a gas, in particular along with air, is fed as a combustion medium to said engine via a gas supply on the fuel medium inlet.

According to an advantageously embodiment of the invention, the working medium of the steam circuit is water or a water mixture. In particular, when designing the internal combustion engine as a gas engine, this results in the advantage that the working medium is not decomposed at high exhaust gas temperatures, which are generated by such a gas engine and on the other hand with a condensation in the temperature range of 80° C. to 99° C. at ambient pressure, the heat drawn from the exhaust gas which is fed to the working medium, can still be used quite well for a cogeneration at normal temperature level. For that purpose, according to a first embodiment, the heat carrier flow, which is used for cooling the internal combustion engine, is simultaneously the working medium of the steam circuit and in particular at the same time the medium fed in the energy recovery system in a closed circuit or the open flow. Alternately, the condensation heat of the working medium of the steam circuit is transferred to the heat carrier flow via a heat exchanger, in this instance designated as a second heat exchanger, whereas the second heat exchanger can form the condenser for instance partially or completely.

A working medium storage tank can be provided in the steam circuit to compensate for leaks and/or volume fluctuations of the working medium. According to an embodiment, the working medium storage tank is designed as a tank through which flows the working medium, that is to say with a working medium inlet, in which in particular all the working medium circulated in the steam circuit by means of the feed pump flows in permanently, and with a working medium outlet, via which said working medium again flows out of the working medium storage tank.

The internal combustion engine and the reciprocating piston expander operate advantageously at the same rotational speed level, in particular, the drive shafts or the crankshafts of both machines rotate essentially or precisely with the same rotational speed. Both machines, both are advantageously designed as reciprocating piston machines, drive according to an embodiment together one and the same generator, or in case of a plurality of generators provided, the same generators.

The reciprocating piston expander can by way of example be designed as a two-cylinder, three-cylinder, four-cylinder, five-cylinder or six-cylinder machine. The same goes for the internal combustion engine.

If the internal combustion engine is designed as a gas engine, bio gas, in particular natural gas, landfill gas, wood gasification gas or sewage gas can be an appropriate combustion medium. Other combustion media are however possible.

The whole steam circuit and its integration into the power plant can be controlled and/or monitored by a common system control. Hereby, a heavy-duty low-maintenance system with closed circuit, self-regulating control system and adaptable to the different internal combustion engines is achievable.

The invention will now be described by way of example using an embodiment.

In FIG. 1 an internal combustion engine 1, here in the form of a gas engine, comprising a fuel medium inlet 2 and an exhaust gas outlet 3 is disclosed.

On the one hand air from an air inlet 4 and on the other hand gas from a gas tank 5 are fed for common combustion to the internal combustion engine 1 via a fuel medium supply 19 connected to a fuel medium inlet 2. Hot exhaust gas flows via the exhaust gas outlet 3 first of all via a heat exchanger 6, by means of which a heat carrier flow 7, in particular a cooling water flow, is heated up, and subsequently via a heat exchanger 8, which works as an evaporator for the working medium of a steam circuit 9. The exhaust gas flow itself is designated in this case by 10.

The working medium of the steam circuit 9 is pumped by means of a feed pump 11, which is driven by the reciprocating piston expander 12, through the heat exchanger 8, evaporated there and then flows into the reciprocating piston expander 12, in which it expands to produce mechanical work. The internal combustion engine 1 respectively its crankshaft is driven by means of this mechanical work, which drives the generator 13 again by using the mechanical work produced in the internal combustion engine 1. The generator 13 feeds the electric current which it produces into an electrical grid 14.

The working medium expanded in the reciprocating piston expander 12 flows through a condenser 15, in which it is condensed, and further through the working medium storage tank 16 back into the feed pump 11.

The condenser 15 is simultaneously a second heat exchanger in the heat carrier flow 7 and transfers the condensation heat to the heat carrier flow 7, so as to heat the same, before the heat carrier flow 7 is fed to a energy recovery system 17, for instance a local heating network, a district heating network or a process heating network. The heat carrier flow 7 can, as represented, be guided as an flow or, as is illustrated by the dotted line, as a closed circuit.

It goes without saying that the sequence of the heat exchangers 6, 15 could be reversed in the heat carrier flow 7 or additional heat exchangers could be provided in the power plant for inputting heat into the heat carrier flow 7, for instance in an exhaust gas recirculation of the internal combustion engine 1 (not represented).

In this instance, the reciprocating piston expander 12 is connected to the internal combustion engine 1 via a releasable clutch 18, whereas the clutch 18 according to a first embodiment can be released or closed only at standstill and according to an alternative form of embodiment also during operation of the internal combustion engine 1 and/or of the reciprocating piston expander 12.

In deviation from the embodiment represented, the feed pump 11 could also be driven by the internal combustion engine 1 or by an additional unit, such as an electric motor.

The invention claimed is:

1. A stationary power plant for generating electricity, the stationary power plant comprising:
an internal combustion engine comprising a fuel medium inlet and an exhaust gas outlet, wherein an exhaust gas flow of the internal combustion engine is discharged via the exhaust gas outlet;
an electrical generator driven by the internal combustion engine to generate electricity, wherein the electrical generator is coupled or can be coupled to an electrical grid, in order to feed the generated electricity into, said grid;
a fuel medium supply connected to the fuel medium inlet;
wherein a steam circuit having a working medium circulated using a feed pump, the steam circuit comprising a heat exchanger arranged in the exhaust gas flow for transferring waste heat of the exhaust gas flow to the working medium for partially or completely evaporating the working medium, the steam circuit further comprising a condenser, in which the working medium partially or completely condenses;
wherein the steam circuit includes a reciprocating piston expander is, in which the working medium expands to produce mechanical work, and the reciprocating piston expander is connected to at least one of the internal combustion engine and the electrical generator using a releasable clutch:

wherein the internal combustion engine is a gas engine, and a gas supply is connected to the fuel medium inlet to supply a gas, and wherein the gas along with air act as a combustion medium of the gas engine.

2. The stationary power plant according to claim 1, wherein a cogeneration of heat and power is provided, comprising a heat carrier flow being a cooling water flow, by means of which the internal combustion engine is cooled, and which is supplied to a local heating network, district heating network, process heating network or other heat recovery system, wherein the heat carrier of the heat carrier flow is simultaneously the working medium of the steam circuit.

3. The stationary power plant according to claim 1, wherein a working medium storage tank is provided in the steam circuit, which is designed as a tank through which flows the working medium.

4. The stationary power plant according to claim 1, wherein the crankshaft is directly connected to a crankshaft of the internal combustion engine.

5. The stationary power plant according to claim 1, wherein the working medium is water or a water mixture.

6. The stationary power plant according to claim 5, wherein a cogeneration of heat and power is provided, comprising a heat carrier flow being a cooling water flow, by means of which the internal combustion engine is cooled, and which is supplied to a local heating network, district heating network, process heating network or other heat recovery system, wherein the heat carrier of the heat carrier flow is simultaneously the working medium of the steam circuit.

7. The stationary power plant according to claim 1, wherein the reciprocating piston expander includes a crankshaft connected to a crankshaft of the internal combustion engine.

8. The stationary power plant according to claim 7, wherein a cogeneration of heat and power is provided, comprising a heat carrier flow being a cooling water flow, by means of which the internal combustion engine is cooled, and which is supplied to a local heating network, district heating network, process heating network or other heat recovery system, wherein the heat carrier of the heat carrier flow is simultaneously the working medium of the steam circuit.

9. The stationary power plant according to claim 5, wherein the reciprocating piston expander includes a crankshaft connected to a crankshaft of the internal combustion engine.

10. The stationary power plant according to claim 9, wherein a cogeneration of heat and power is provided, comprising a heat carrier flow being a cooling water flow, by means of which the internal combustion engine is cooled, and which is supplied to a local heating network, district heating network, process heating network or other heat recovery system, wherein the heat carrier of the heat carrier flow is simultaneously the working medium of the steam circuit.

11. The stationary power plant according to claim 1, wherein a cogeneration of heal and power is provided, comprising a heat carrier flow being a cooling water flow, by means of which the internal combustion engine is cooled, and which is supplied to a local heating network, district heating network, process heating network or other heat recovery system, wherein a second heat exchanger is provided in the heat carrier flow, which is subjected to the condensation heat of the working medium so as to heat up the heat carrier flow.

12. The stationary power plant according to claim 11, wherein the second heat exchanger partially or completely forms the condenser.

13. The stationary power plant according to claim 1, wherein the combustion medium is a bio gas.

14. The stationary power plant according to claim 13, wherein the bio gas is one of a natural gas, a landfill gas, a wood gasification gas and a sewage gas.

* * * * *